(12) United States Patent
Gurjar et al.

(10) Patent No.: US 8,569,544 B2
(45) Date of Patent: Oct. 29, 2013

(54) PROCESS FOR PREPARATION OF BENZPHETAMINE AND ITS PHARMACEUTICALLY ACCEPTABLE SALTS

(75) Inventors: Mukund Keshav Gurjar, Pune (IN); Narendra Kumar Tripathy, Pune (IN); Kiran Avinash Bapat, Pune (IN); Vemavarapu P. K. V. Rao, Pune (IN); Satyajeet Binay Biswas, Pune (IN); Samit Satish Mehta, Pune (IN)

(73) Assignee: Emcure Pharmaceuticals Limited, Pune (IN)

( * ) Notice: Subject to any disclaimer, the term of this patent is extended or adjusted under 35 U.S.C. 154(b) by 520 days.

(21) Appl. No.: 12/858,779

(22) Filed: Aug. 18, 2010

(65) Prior Publication Data

US 2011/0046416 A1 Feb. 24, 2011

(30) Foreign Application Priority Data

Aug. 19, 2009 (IN) .......................... 1905/MUM/2009

(51) Int. Cl.
*C07C 211/00* (2006.01)
(52) U.S. Cl.
USPC ............ 564/381; 564/305; 564/391; 514/655

(58) Field of Classification Search
None
See application file for complete search history.

(56) References Cited

U.S. PATENT DOCUMENTS

| 2,789,138 | A | 4/1957 | Heinzelman et al. |
|---|---|---|---|
| 5,536,877 | A | 7/1996 | Hammer et al. |
| 7,456,318 | B2 | 11/2008 | Kalota |
| 7,750,187 | B2 | 7/2010 | Kalota et al. |
| 2009/0124833 | A1* | 5/2009 | Tomazi .......................... 564/366 |

FOREIGN PATENT DOCUMENTS

| WO | WO-2006-057778 A2 | 6/2006 |
|---|---|---|
| WO | WO-2008-048254 A1 | 4/2008 |

* cited by examiner

*Primary Examiner* — Sudhakar Katakam
(74) *Attorney, Agent, or Firm* — Blank Rome LLP

(57) ABSTRACT

The present invention provides a simple method for preparation of benzphetamine and its acid addition salt comprising reaction of methamphetamine hydrochloride of formula (III) with benzyl chloride and treating the isolated benzphetamine of formula (II) with an acid dissolved in an organic solvent to provide benzphetamine acid addition salt, more specifically, benzphetamine hydrochloride of formula (I).

14 Claims, No Drawings

PROCESS FOR PREPARATION OF BENZPHETAMINE AND ITS PHARMACEUTICALLY ACCEPTABLE SALTS

This application claims priority under 35 U.S.C. §119 to Indian Patent Application No. IN 1905/MUM/2009, filed Aug. 19, 2009, which is hereby incorporated by reference in its entirety.

FIELD OF THE INVENTION

The present invention relates to a process for preparation of Benzphetamine and its pharmaceutically acceptable salt in high yield and purity. More, specifically, the invention relates to a novel method of benzylation for synthesis of Benzphetamine.

BACKGROUND OF THE INVENTION

Benzphetamine hydrochloride of formula (I), chemically known as (2S)-N-benzyl-N-methyl-1-phenylpropan-2-amine is an amphetamine derivative exhibiting appetite suppressant activity and is utilized for long term management of obesity under the brand name Didrex. The drug was first synthesized by Heinzelman et.al. (U.S. Pat. No. 2,789,138) and found to be a superior bronchodilator and a CNS stimulator, which increases heart rate and blood pressure.

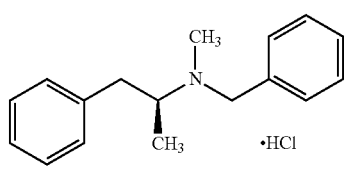

(I)

U.S. Pat. No. 2,789,138 discloses a method for preparation of benzphetamine hydrochloride (I) by reaction of benzyl chloride with dextromethamphetamine (d-desoxyephedrine) in the presence of a base such as sodium carbonate and in an inert organic solvent such as benzene, toluene, xylene etc. The preliminary effort for preparing the hydrochloride salt comprised of dissolving the benzphetamine free base of formula (II) in ethyl acetate followed by treatment with ethanolic hydrogen chloride. However, the hydrochloride salt thus formed was reported to have a melting point of 129° C. to 130° C. The document does not mention either the yield or the purity of the final product thus obtained. Current literature however indicates that benzphetamine has a melting point between 152° C. and 153° C. (Merck Index, 10$^{th}$ edition). The higher melting point reported in current literature suggests that the product thus obtained was highly impure and required several purifications which would eventually reduce the final yield and was thus not suitable for commercial scale.

U.S. Pat. No. 5,536,877 discloses a process for preparation of aryl benzyl amines by reaction of aryl amines with benzyl chloride in the presence of an inorganic base and a phase transfer catalyst like tetrabutylammonium chloride. The reaction was carried out at an elevated temperature range of 90° C. to 110° C. with the reaction time of about 24 hours which is abnormally long even in the presence of a phase transfer catalyst. Further, there was no disclosure about the isolation method or the yield or purity of the final product.

U.S. Pat. No. 7,456,318 discloses a process for preparation of benzphetamine by reaction of an excess of methamphetamine with benzyl chloride. Methamphetamine was employed in a molar ratio of 2:1 with respect to benzyl halide for scavenging the by-product hydrogen halide formed during the reaction. Further, due to the precipitation of the hydrogen halide salt of methamphetamine during the reaction, the reaction mixture became too viscous for effective agitation and had to be diluted with a solvent such as toluene. The hydrogen halide salt of the reactant also had to be separated before allowing the reaction to proceed further.

Benzphetamine (II) obtained during the reaction was then treated with concentrated hydrochloric acid. The hydrochloride salt (I) thus obtained was an oil, which had to be crystallized after azeotropic removal of water and further cooling. It is pertinent to mention that the product of formula (I) thus obtained has about 4.3% of the starting material and required to be purified further for obtaining the desired purity for conforming to regulatory specifications, thereby reducing the overall yield considerably.

A crystallization method for obtaining crystalline benzphetamine hydrochloride is disclosed in U.S. Pat. No. 7,750,187 and comprises addition of benzphetamine hydrochloride usually obtained as oil in an organic solvent such as toluene to form a biphasic mixture, removing water and crystallizing benzphetamine hydrochloride and separating the crystalline benzphetamine hydrochloride from the organic medium. The method utilizes a Dean-Stark apparatus for removal of water. Further, the crude benzphetamine hydrochloride which was obtained as an oil had to be recrystallized from a mixture of ethyl acetate and isopropanol followed by another recrystallization utilizing ethyl acetate, in order to obtain the desired purity. Thus the effective yield for obtaining a crystalline solid from benzphetamine hydrochloride oil was only about 70%. Thus, there was considerable loss during the reprocessing thereby, rendering the method uneconomical and unfeasible for commercial exploitation.

WO 2008048254 also discloses a process for preparation of highly pure crystalline benzphetamine hydrochloride by utilizing ethyl acetate in association with an organic modifier such as ethanol, methanol, isopropanol and n-butanol. The method involved initial crystallization of benzphetamine hydrochloride oil from ethyl acetate followed by further crystallization of the product from a binary mixture of ethyl acetate and an alcohol. The yields obtained herein also were between 55-70%, which was not suitable for commercial scale.

Another method for purification of WO 2006057778 involves removal of the methamphetamine impurity in an aqueous medium having a pH range of 6-8, however herein also the step of obtaining a crystalline product involved azeotropic removal of water with toluene as solvent. The yield obtained was only 70%; thus the method was uneconomical due to the multiple steps of purification and crystallization.

Therefore, to overcome the problems associated with the above prior art methods, there was a need to develop a simple, efficient, high yielding process which requires a short period of time and does not result in unreacted starting material remaining at the end of the reaction, with increased yield and have minimal impurities. Further, there is a need for a process which yields benzphetamine hydrochloride salt of formula (I) as a crystalline solid and not as an oil, without requiring any additional purification steps.

OBJECT OF THE INVENTION

An object of the invention is to provide a simple process for preparation of Benzphetamine of formula (II).

Another object of the invention is to provide a process for preparation of Benzphetamine of formula (II), which does not require a phase transfer catalyst for reaction completion.

Yet another object of the invention is to provide a process for preparation of Benzphetamine hydrochloride of formula (I) as a crystalline material and not as an oil without an additional step of purification.

A further object of the present invention is to provide benzphetamine hydrochloride salt of formula (I) in high yields with purity conforming to regulatory specifications.

SUMMARY OF THE INVENTION

An aspect of the present invention relates to a process for preparation of Benzphetamine and its pharmaceutically acceptable acid addition salt comprising:

i) reaction of methamphetamine of formula (III) with benzyl chloride in the presence of a mild base and water and isolating benzphetamine of formula (II);

ii) treatment with an acid in an organic solvent; and iii) isolation of benzphetamine acid addition salt.

Another aspect of the present invention relates to a process for preparation of Benzphetamine hydrochloride salt of formula (I) comprising reaction of methamphetamine hydrochloride of formula (III) with benzyl chloride in water, in the presence of an inorganic base and isolating benzphetamine of formula (II) followed by subsequent treatment with hydrochloric acid in an organic solvent in anhydrous conditions and isolating benzphetamine hydrochloride salt of formula (I).

DETAILED DESCRIPTION OF THE INVENTION

The present invention relates to a process for preparation of benzphetamine and its pharmaceutically acceptable salts.

In an embodiment of the invention, the process for preparation of Benzphetamine and its acid addition salt comprises i) reaction of methamphetamine hydrochloride of formula (III) with benzyl chloride in water, in the presence of a mild base at an elevated temperature to provide benzphetamine of formula (II), ii) treating benzphetamine base of formula (II) with an acid in an organic solvent and in anhydrous conditions to give Benzphetamine acid addition salt of formula (I).

The reaction for preparation of hydrochloride salt can be schematically represented as follows:

Scheme: Method of the present invention for preparation of benzphetamine hydrochloride salt (I) from methamphetamine hydrochloride (III)

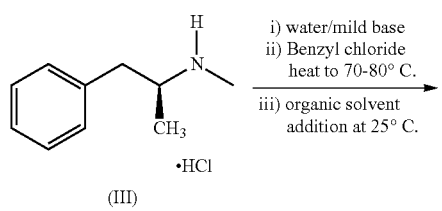

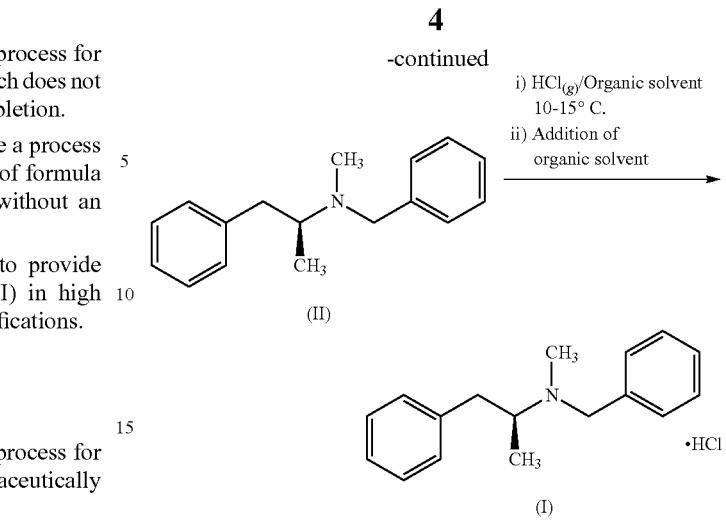

The preparation of Methamphetamine hydrochloride of formula (III) is disclosed in copending application no. 1582/MUM/2009, which is incorporated herein as a reference.

According to a preferred embodiment of the invention, methamphetamine hydrochloride of formula (III) is heated with benzyl chloride in the presence of a mild base and water to give Benzphetamine base of formula (II).

The mild base is either an inorganic or an organic base, but preferably an inorganic base. The inorganic base can be selected from the group comprising of sodium carbonate, potassium carbonate, cesium carbonate and the like. A preferred base is potassium carbonate.

The reaction could also be carried out in inert organic solvents like ethers such as tetrahydrofuran, nitriles like acetonitrile and amides like dimethyl formamide, dimethyl acetamide, aromatic hydrocarbons like toluene but the reaction is facile in water as compared to the inert organic solvents resulting in improved yield and desired purity. Therefore, the preferred solvent is water.

The reaction is carried out by heating the reaction mixture at a temperature ranging between 70° C. and 80° C., preferably at 75±2° C.

After completion of the reaction, as monitored by HPLC, the benzphetamine base of formula (II) present in the reaction mixture is cooled and the isolation is carried out by adding an organic solvent. Suitable organic solvents include, but are not limited to, aromatic hydrocarbons and aliphatic hydrocarbons, preferably with an aromatic hydrocarbon like toluene. The reaction mixture is cooled to 25° C. and toluene is added with stirring. The toluene layer is separated and concentrated to give quantitative yield of benzphetamine free base.

It should be noted that the reaction is quite facile and proceeds toward completion without any unreacted starting material thereby circumventing the additional steps of purification and avoiding any loss in yield to give the benzphetamine free base in quantitative yield.

Benzphetamine base of formula (II) is then converted to its hydrochloride salt by treatment with anhydrous hydrochloric acid.

In a preferred embodiment, Benzphetamine hydrochloride (I) is prepared by treating benzphetamine base (II) with anhydrous hydrochloric acid dissolved in a organic solvent such as an ester selected from ethyl acetate, methyl acetate, isobutyl acetate and the like.

Preferably, ethyl acetate containing 10% HCl (w/w) is added to the crude Benzphetamine free base at a temperature ranging between 10-15° C. Excess hydrochloric acid gas is removed by concentration of the solvent. Surprisingly, the product obtained is a crystalline solid and not an oil as disclosed in the prior art. The mixture is cooled to 0-5° C. and ethyl acetate is added to the mixture and stirred for 1 hour at 25° C. The solid obtained is filtered, washed with ethyl acetate and dried.

The hydrochloride salt formation step is carried out in anhydrous conditions which give Benzphetamine hydrochloride directly in a solid crystalline form and in quantitative yield with the desired purity and the impurity profile conforming to regulatory guidelines. It should be noted that further purification of the product is not required thereby making the process cost effective.

Thus, in one embodiment of the present process for preparation of Benzphetamine Hydrochloride, benzylation of methamphetamine HCl is carried out under mild conditions using mild base and in water, thereby giving benzphetamine in high yield and with desired purity unlike prior art methods which utilize organic solvents and thus, additional cost and heavy load on the effluent, is avoided.

In another embodiment of the present invention, during the preparation of the hydrochloride salt, hydrochloric acid gas dissolved in ethyl acetate is used for the preparation of benzphetamine hydrochloride salt which results in the formation of the hydrochloride salt in a solid crystalline form. Prior art methods gave the hydrochloride salt in the form of an oil which needed further processing thereby making the overall process lengthy and cumbersome. Thus, the present process is simple and avoids a further step of purification, thereby increasing the overall yield.

The benzphetamine free base which is obtained from the abovementioned process has a purity ≥98% and is formed in quantitative yield which is directly converted to the corresponding acid addition salt in highly purified form with quantitative yield and without any further purification.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

EXAMPLES

Example 1

Preparation of Benzphetamine Free Base

Distilled mineral water (1400 ml) was added to methamphetamine hydrochloride (280 g) at 25° C. and stirred to dissolve. Potassium carbonate (624 gms; 3.0 eq) was added to the mixture and was stirred for 30 min. Benzyl chloride (225.5 ml, 1.1 eq) was added to the reaction mixture at 25° C. The reaction mixture was heated to 75° C. and was monitored by TLC. After completion of the reaction the mixture was cooled to 25° C. Toluene (1400 ml) was added to the mixture and stirred for 30 minutes at ambient temperature. The toluene layer was separated and concentrated under reduced pressure at 55° C.-60° C. to give Benzphetamine free base.
Yield: Quantitative.
Purity: ≥98% by HPLC.

Example 2

Preparation of Benzphetamine Hydrochloride

Ethyl acetate (810 ml) containing 10% HCl was added to the crude benzphetamine free base isolated from Example 1 at 10-15° C. The mixture was stirred for 30 min at 10-15° C. and then stirred at 25°~30° C. for 8-10 hours. Excess hydrochloric acid gas was removed by concentration of the solvent to give a solid. The reaction mass was cooled to 0-5° C. Ethyl acetate (1500 ml) was added to the mixture and was stirred for 1 h at 25° C. The solid obtained was filtered and was washed with ethyl acetate (1000 ml). The solid obtained was dried for 6 h under vacuum at 55° C.-60° C.
Yield: ≥98%.
HPLC Purity: >99%
Chiral purity: >99% e.e.

The invention claimed is:
1. A process for the preparation of an acid addition salt of benzphetamine comprising
   a) i) reacting methamphetamine hydrochloride of formula (III)

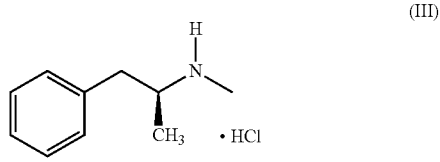

with benzyl chloride in the presence of a mild base and water at a temperature between 70 and 80° C. to form a reaction mixture, and
   ii) isolating benzphetamine of formula (II) from the reaction mixture

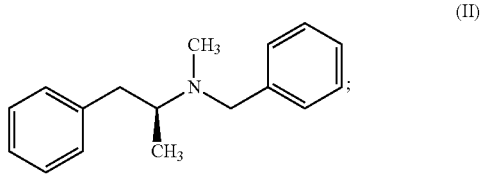 [SMILES: C[C@@H](Cc1ccccc1)N(C)Cc1ccccc1]

b) treating the benzphetamine of Formula (II) with an acid in an organic solvent to form a second reaction mixture; and
   c) isolating the acid addition salt of benzphetamine from the second reaction mixture.
2. A process according to claim 1, wherein the acid addition salt is a hydrochloride salt.
3. A process according to claim 1 wherein the mild base is an inorganic base.
4. A process according to claim 1, wherein the temperature of step (a) is between 73 and 77° C.
5. A process according to claim 1, wherein the benzphetamine of formula (II) formed in step (a) is isolated by cooling the reaction mixture to ambient temperature, adding an aromatic hydrocarbon and concentrating the organic layer.

6. A process according to claim 1, wherein the organic solvent in step (b) is an ester.

7. A process according to claim 6, wherein the ester is ethyl acetate.

8. A process according to claim 1, wherein the acid addition salt of benzphetamine is isolated by concentrating the second reaction mixture, adding an ester solvent at 0-5° C. and filtering.

9. A process according to claim 2, wherein the benzphetamine hydrochloride is isolated by concentrating the second reaction mixture, adding an ester solvent at 0-5° C. and filtering.

10. A process for the preparation of benzphetamine hydrochloride comprising:
a) reacting methamphetamine hydrochloride of formula (III)

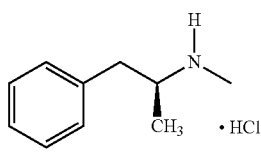

with benzyl chloride in the presence of potassium carbonate and water at a temperature of 75±2° C.;
b) i) adding toluene and
ii) isolating benzphetamine of formula (II) by concentrating the organic layer,

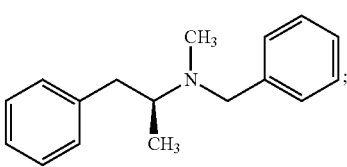

c) i) treating the benzphetamine of formula (II) with anhydrous hydrochloric acid in ethyl acetate under anhydrous conditions to form a reaction mixture,
ii) concentrating the reaction mixture, and
iii) adding an ester solvent; and
d) isolating benzphetamine hydrochloride salt of formula (I)

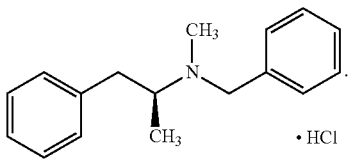

11. The process according to claim 1, wherein the acid addition salt is a pharmaceutically acceptable acid addition salt.

12. The process according to claim 3, wherein the inorganic base is selected from sodium carbonate, potassium carbonate, and cesium carbonate.

13. A process for the preparation of benzphetamine of formula (II)

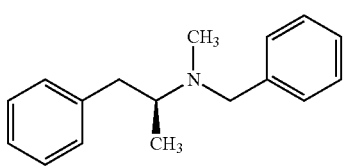

comprising reacting methamphetamine hydrochloride of formula (III)

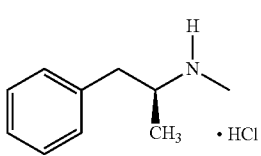

with benzyl chloride in the presence of a mild base and water at a temperature between 70 and 80° C.

14. The process of claim 13, further comprising converting the benzphetamine of formula (II) to an acid addition salt of benzphetamine.

* * * * *